United States Patent [19]
Hurlburt

[11] Patent Number: 5,658,344
[45] Date of Patent: Aug. 19, 1997

[54] TIBIAL INSERT REINFORCEMENT PIN

[75] Inventor: Robert C. Hurlburt, Whitman, Mass.

[73] Assignee: Johnson & Johnson Professional, Inc., Raynham, Mass.

[21] Appl. No.: 581,038

[22] Filed: Dec. 29, 1995

[51] Int. Cl.$^6$ ................................. A61F 2/38
[52] U.S. Cl. ............................. 623/20; 623/18
[58] Field of Search .............. 623/20, 18; 411/180, 411/338, 339, 508, 509, 510, 456; 24/580, 585, 707.6

[56] References Cited

U.S. PATENT DOCUMENTS 5,007,933   4/1991   Sidebotham ..................... 623/20

OTHER PUBLICATIONS

Johnson & Johnson Orthopaedics, "P.F.C.® Modular Knee System", 1994.
Johnson & Johnson Orthopaedics, "P.F.C.® Modular Total Knee System", 1992.
Johnson & Johnson Orthopaedics Brochure entitled P.F.C.® Modular Knee System: Research Data and Laboratory Testing, Braintree, MA, 1989 (4 pp).

Primary Examiner—David Isabella
Assistant Examiner—John M. Black
Attorney, Agent, or Firm—Nutter, McClennen & Fish, LLP

[57] ABSTRACT

A knee prosthesis includes a femoral component, a patella insert, a tibial bearing insert, a tibial tray and a reinforcement pin. The reinforcement pin is constructed such that it includes a ribbed region comprised of one or more circumferentially oriented ribs. The diameter of the ribbed region of the pin exceeds that of the non-ribbed region of the pin. The reinforcement pin is adapted to seat within a bore formed in the tibial bearing insert in an interference fit. A distal portion of the pin protrudes from the inferior surface of the tibial bearing insert and is adapted to fit, in a clearance fit, within a bore formed in a superior surface of the tibial tray.

15 Claims, 3 Drawing Sheets

TIBIAL INSERT REINFORCEMENT PIN

BACKGROUND OF THE INVENTION

The invention relates to knee joint prostheses and more particularly to knee joint prostheses and components thereof having improved fixation and stability of the tibial bearing insert to the tibial tray.

Joint replacement surgery is quite common and enables many individuals to function normally when otherwise it would not be possible to do so. Artificial joints are normally composed of metallic, ceramic and/or plastic components that are fixed to existing bone.

Knee arthroplasty is a well known surgical procedure by which a diseased and/or damaged natural knee joint is replaced with a prosthetic knee joint. Typical knee prostheses include a femoral component, a patella component, a tibial tray or plateau, and a tibial bearing insert. The femoral component generally includes a pair of laterally spaced apart condylar portions, the distal surfaces of which articulate with complementary condylar elements formed in a tibial bearing insert.

The tibial tray is mounted within the tibia of a patient. Typically, the tibial bearing insert, which is usually made of ultrahigh molecular weight polyethylene (UHMWPE), is mounted upon the superior surface of the tibial tray through mechanical interlocking. Load and stress is placed on the knee prosthesis, and particularly on the tibial bearing insert, during normal daily use and may lead to displacement or dislocation of the insert from the tibial tray. Tibial bearing inserts that are specifically designed for revision knee prostheses as well as those designed to compensate for colleratal ligament deficiency are particularly susceptible to loads and stresses that could cause dislocation or displacement of the tibial bearing insert. Such inserts usually have a protruding eminence on the superior surface of the insert, which is designed to limit varus and valgus movements of the knee joint. In deep flexion of the joint (e.g., 90°–120° ) the femoral component exerts a high anteriorly directed load component on a posterior facing wall of the eminence. As noted above, this force component can lead to dislocation or displacement of the tibial bearing insert.

Several techniques are known to reinforce or mate the tibial bearing insert to the tibial tray. For example, U.S. Pat. No. 4,822,366 affixes the tibial bearing insert to the tibial tray using a nut and a cooperating bolt. A similar design, which relies upon a threaded locking screw to reinforce the mating of the tibial bearing insert and the tibial tray, is disclosed in U.S. Pat. No. 4,936,853.

Other reinforcement designs rely upon threaded screws to help secure the tibial insert to the tibial tray. One disadvantage of such designs is the potential that the threading of the screw through the polymeric insert could increase the potential for developing wear debris within the joint. Wear debris results as minute particles of debris (e.g., metal or plastic from the prosthesis) become dislodged and migrate within the joint. The phenomenon of wear debris within artificial joints is a serious problem that can inhibit the proper mechanical functioning of the joint. Moreover, wear debris can lead to osteolysis and bone deterioration. When wear debris develops within an artificial joint, surgical removal of the debris or subsequent replacement of the artificial joint is often necessary.

There is thus a need to provide alternative mechanisms and devices for reinforcing the securement of a tibia/bearing insert to a tibial tray in a knee prosthesis.

Accordingly, it is an object of the present invention to provide knee prostheses in which securement of the tibial bearing insert to the tibial tray is reinforced. A further object is to provide an effective reinforcing pin that reduces the load exerted on the tibial bearing insert by the femoral component. It is also an object to provide a knee prosthesis in which some of the load directed to the tibial bearing insert can be transferred to the tibial tray. Another object is to provide a reinforcement pin for increasing the strength of attachment of the tibial bearing insert to the tibial tray. It is also an object to provide improved knee prostheses that are better able to withstand the forces associated with normal daily activities. These and other objects of the invention will be apparent to those having ordinary skill in the art upon reading the disclosure that follows.

SUMMARY OF THE INVENTION

The invention provides a knee joint prosthesis exhibiting reinforced joinder of the tibial bearing insert to the tibial tray, and improved stability of the tibial bearing insert. This is achieved using a reinforcing pin, one end of which is virtually permanently secured within the tibial bearing insert and the other end of which is disposed within the tibial tray in a floating mount.

The reinforcing pin is effective in that it decreases the susceptibility of the tibial bearing insert to forces exerted by the femoral component that could have the tendency to displace or dislocate the tibial bearing insert. In deep flexion of the knee joint forces are exerted by the femoral component on the tibial bearing insert in a direction transverse to the axis of the reinforcement pin. Thus, these forces are effectively transferred through the reinforcement pin to the adjacent tibial tray and have little, if any, adverse effect upon the tibial bearing insert.

A knee prosthesis constructed according to the present invention includes a tibial tray component that has an inferior end adapted to mount within the tibia of a patient and a superior surface including mechanical interlocking features that cooperate with corresponding features on a tibial bearing insert to mechanically join the tibial tray to the tibial bearing insert. A tibial bearing insert, the inferior surface of which mechanically interlocks and fits within the superior surface of the tibial tray, includes a superior bearing surface having condylar portions that are adapted to seat and articulate with condyle elements of a femoral component of a knee prosthesis. A first bore extends partially into the tibial bearing insert from the inferior surface thereof. Preferably, the first bore is positioned substantially at the midpoint of the bearing insert between the lateral and medial edges thereof, and slightly anterior of the midpoint between the anterior and posterior edges thereof. In one embodiment a second bore is formed within the superior surface of the tibial tray. The first and second bores are in substantial alignment with one another when the tibial bearing insert and the tibial tray are matingly engaged.

The knee prosthesis of the invention also includes an elongate reinforcement pin having a first; proximal end and a second, distal end. The pin includes a ribbed region having one or more circumferentially oriented ribs disposed distal of the first end of the pin. Preferably, the diameter of the pin in the ribbed region is slightly greater than the diameter of the pin in at least the non-ribbed region of the pin proximal of the ribbed region. In a preferred embodiment, the diameter of the ribbed region of the pin is greater than the diameter of the non-ribbed region of the pin.

Each rib formed in the reinforcement pin is of a substantially triangular shape in cross-section. Each rib has a proximal-facing surface that is canted and a distal-facing surface that is substantially transverse to the longitudinal axis of the pin. The angle (α) defined by the outer surface of the pin proximal of the ribbed region and the canted, proximal-facing surface of each rib is in the range of about 110° to about 175°. Preferably, this angle is in the range of approximately 150°–160°.

The diameter of the first and second bores is substantially equal. In a preferred embodiment, the diameter of the bores is slightly larger than the diameter of the non-ribbed region of the reinforcement pin in order to allow the non-ribbed portion of the reinforcement pin to fit freely therein. Preferably, there is approximately 0.001 to 0.005 inch clearance between the non-ribbed region of the reinforcement pin and the first and second bores.

The reinforcement pin is adapted to be mounted within the first bore, and thus within the tibial bearing insert, in an interference and/or mechanical fit. To accomplish this, the diameter of the pin in the ribbed region must be slightly greater than the diameter of the first bore. Preferably, the diameter of the ribbed region of the pin exceeds the diameter of the bore by about 0.001 to 0.017 inch to achieve an interfering mechanical fit. When the pin is forced within the first bore the ramped surfaces of the ribbed region of the pin enable the pin to be inserted therein while parting the material from which the insert is formed. When the pin is completely installed within the bore, the material forms around the ramped and non-ramped surfaces of the ribs, causing the pin to be firmly embedded therein. The distal facing surfaces of the ribs generally prevent removal of the pin from the tibial bearing insert.

In a preferred embodiment, once the reinforcement pin is securely embedded within the bore of the tibial bearing insert, the inferior surface of the bearing insert can be mated to the superior surface of the tibial tray. To accomplish this a distal end of the reinforcement pin, which protrudes from the inferior surface of the tibial bearing insert, is disposed within the second bore formed within the superior surface of the tibial tray in a clearance fit. Thereafter, the tibial bearing insert is forced into the tibial tray to effect mating engagement of these two components.

Although the design of the present knee prosthesis is useful for virtually all tibial bearing inserts, it is particularly useful for revision knee prostheses and prostheses that are designed to compensate for collateral ligament deficiencies, and other prostheses which utilize tibial bearing inserts having a raised eminence on the superior surface thereof.

DETAILED DESCRIPTION OF THE INVENTION

Figure 1:
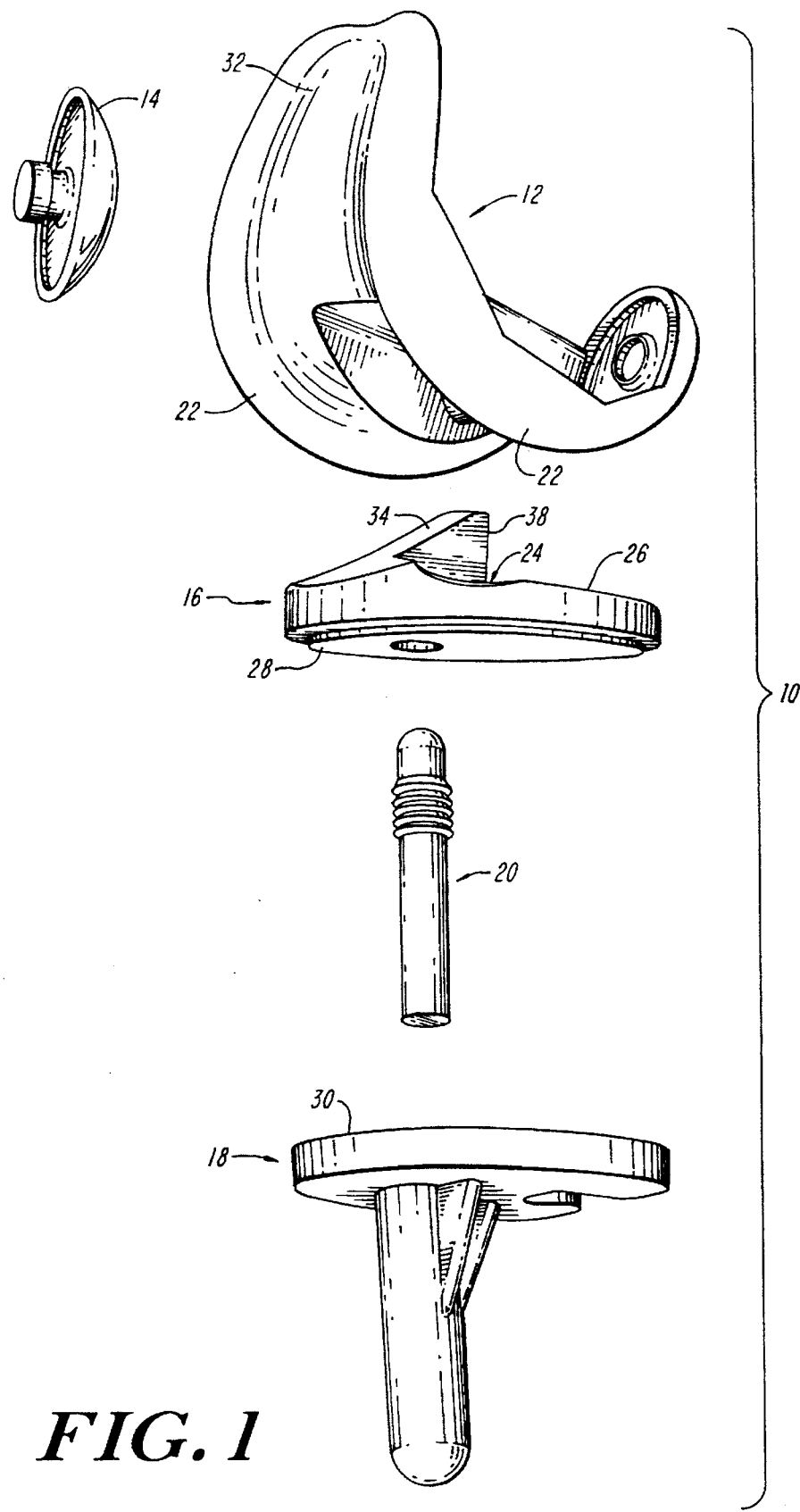
FIG. 1 is an exploded view of a knee prosthesis constructed according to the present invention.

The knee prosthesis 10 of the present invention, as illustrated in FIG. 1, includes a femoral component 12, a patella insert 14, a tibial bearing insert 16, a tibial tray 18, and a reinforcement pin 20. The femoral component includes condyle elements 22 that seat within and articulate with the condyle regions 24 formed on the superior surface 26 of the tibial bearing insert. The patella insert 14 is adapted to seat within and articulate with the patella groove 32 of the femoral component. As is well known in the art, the inferior surface 28 of the tibial bearing insert matingly engages the superior surface 30 of the tibial tray in a secure mechanical fit. The reinforcement pin 20 is adapted to mount within the tibial bearing insert, in a manner described below, to increase the securement of the tibial bearing insert to the tibial tray and to absorb forces imparted by the femoral component that could tend to displace or dislocate the tibial bearing insert.

Figure 2A:
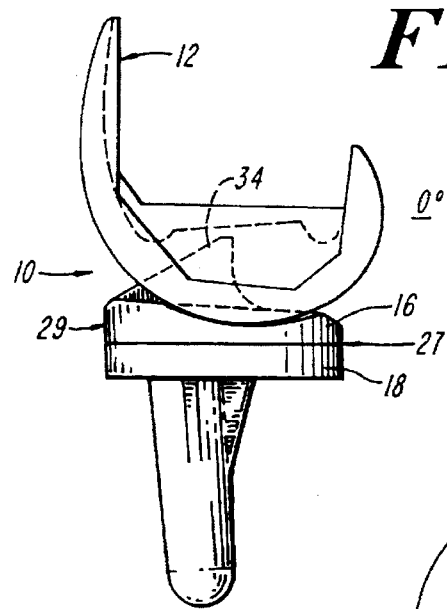
FIG. 2A is a side view of a knee prosthesis of the present invention at 0° flexion.
Figure 2B:
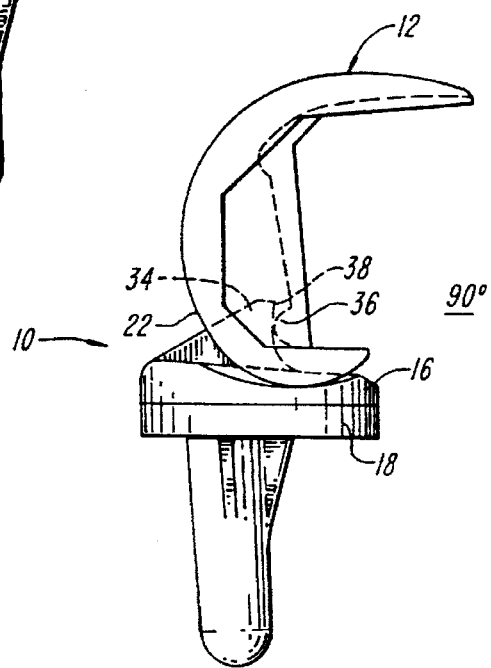
FIG. 2B is a view of the knee prosthesis shown in FIG. 2A at 90° flexion.
Figure 2C:
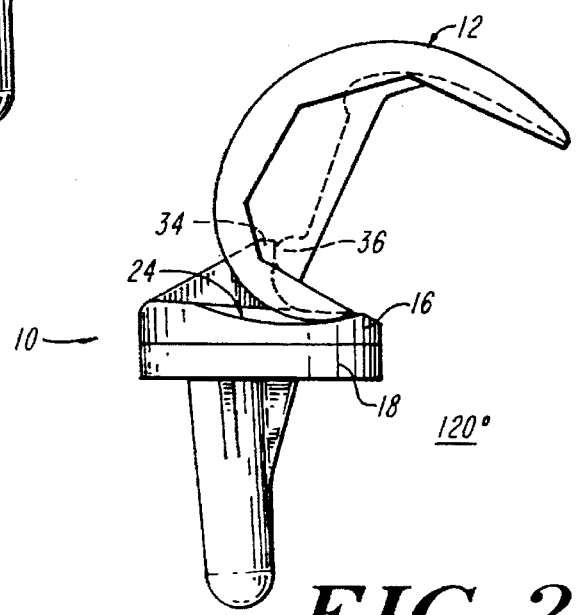
FIG. 2C is a view of the knee prosthesis shown in FIG. 2A at 120° flexion.

FIGS. 2A, 2B, and 2C illustrate the knee prosthesis of the present invention in various degrees of flexion. The illustrated prosthesis has a posterior side 27 and an anterior side 29. For purposes of illustration and discussion, the tibial bearing insert illustrated herein is one which includes a raised eminence 34 formed on the superior surface 26 of the tibial bearing insert. Eminence 34 is typically present in cruciate substituting and revision tibial bearing inserts which are intended to stabilize and/or constrain valgus and varus movements of the knee joint. In conditions of deep flexion (e.g., 90°–120°), as shown in FIGS. 2B and 2C, a posterior cam 36 of the femoral component exerts an anterior directed force on the posterior wall 38 of eminence 34. This force can tend to displace the tibial bearing insert with respect to the tibial tray or, in some cases, to completely dislocate the tibial bearing insert.

The reinforcement pin of the present invention is advantageous since it can reinforce the fixation of the tibial bearing insert to the tibial tray. When properly positioned within the tibial bearing insert and tibial tray, as shown in FIG. 3, the reinforcement pin absorbs and transfers to the tibial tray some of the force exerted by the femoral component, thus rendering the tibial bearing insert less susceptible to displacement or dislocation.

Figure 3:
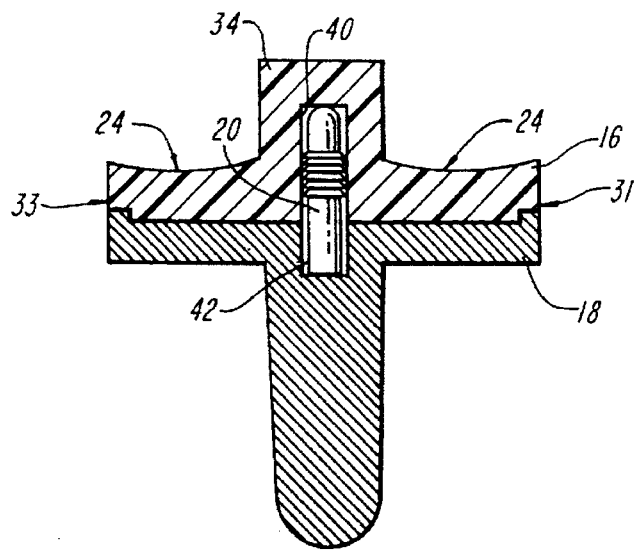
FIG. 3 is a sectional view of the knee prosthesis of claim 2A at lines 3—3.

FIG. 3 illustrates, in cross-section, the mounting of pin 20 within the knee prosthesis of the invention. As shown, a bore 40 extends partially within the tibial bearing insert from the inferior surface thereof. Preferably, the bore extends at least partially into the tibial bearing insert and terminates before the superior surface thereof. In embodiments in which the tibial bearing insert includes a raised eminence 34, the first bore extends partially into the area of the insert occupied by the eminence. As noted above, a second bore 42 extends into the tibial tray 18 from the superior surface thereof. Preferably bores 40, 42 are aligned with one another when the tibial bearing insert is properly mated with the tibial tray. Further, the bores 40, 42 are of substantially the same diameter. In a preferred embodiment the bores have smooth, non-threaded interior walls.

For purposes of illustration, FIG. 3 is assumed to show prosthesis components for a right knee. Thus, the tibial bearing insert has lateral and medial edges 31, 33.

Figure 4:
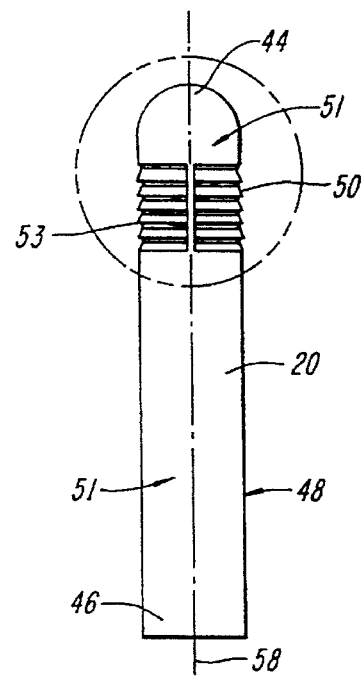
FIG. 4 is a side view of a tibial reinforcement pin constructed according to the present invention.
Figure 5:
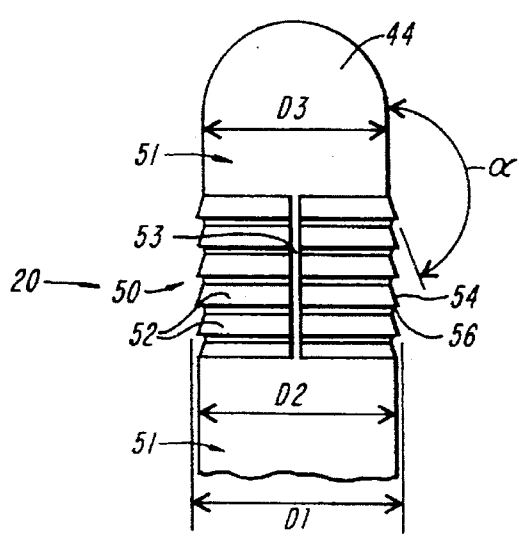
FIG. 5 is a detail view of the proximal portion of the reinforcement pin shown in FIG. 4.

Pin 20, as illustrated in FIGS. 4 and 5, is formed of an elongate member having a first, proximal end 44 and a second, distal end 46. The exterior wall 48 of pin 20 preferably is smooth, except in a ribbed region 50 that is disposed slightly distal of proximal end 44. As further illustrated in FIGS. 4 and 5 the proximal tip 44 of the pin 20 is substantially spherically shaped.

Ribbed region 50 is comprised of one or more ribs 52. Each rib is constructed such that it has a canted proximal facing surface 54 and a distal facing surface 56. Preferably, the distal facing surface 56 is oriented transverse to the longitudinal axis 58 of pin 20. Alternatively, distal facing surface 56 is oriented at an angle of less than 90°, as measured from surface 56 to a portion of the longitudinal axis 58 distal of surface 56. Canted surface 54 preferably extends at an angle ($\alpha$) of between 110° and 175° as measured from canted surface 54 to a portion of the exterior wall 48 of pin 20 proximal to canted surface 54.

As illustrated in FIGS. 4 and 5, pin 20 preferably includes an axial break 53 in ribbed region 50. The axial break is a discontinuity in each rib that facilitates easy insertion of the pin into the bore 40. Axial break preferably is of a depth such that it extends to the nominal base of the rib. The width of break 53 may vary, but is generally in the range of about 0.001 to 0.020 inch.

One of ordinary skill in the art can readily determine the optimal number of fibs 52 that should make up ribbed region 50. Typically, there are between 1 and 15 ribs, and more preferably about 4 to 8 ribs.

The diameter of pin 20 at ribbed region 50 ($D_1$) is greater than the diameter of the pin distal to the ribbed region ($D_2$) and the diameter of the pin proximal to the ribbed region ($D_3$). In a preferred embodiment $D_2$ and $D_3$ are substantially equal. The value for $D_1$ preferably is greater than the values for $D_2$ and/or $D_3$ by about 0.001 to 0.017 inch, and more preferably by about 0.003 to 0.010 inch.

As noted above, bore 40 formed in tibial bearing insert 16 includes smooth inner walls. Bore 40 is dimensioned to accommodate at least the proximal end 44 of pin 20 and/or the entire non-ribbed region 51 of pin 20 in a clearance fit. Preferably, the clearance between the inner walls of the bore and the non-ribbed portion of the pin is about 0.001 to 0.005 inch and most preferably about 0.002 to 0.003 inch. The pin is intended to be disposed within the bore 40 in an interference fit. Thus, the diameter of the ribbed region of the pin (D1) preferably exceeds the diameter of the bore by about 0.001 to 0.017 inch, and most preferably by about 0.002 to 0.008 inch. Those having ordinary skill in the art will appreciate that the degree of interference between the ribbed region of the pin and the bore of the tibial bearing insert may vary depending on the requirements of a given application.

Preferably, tibial bearing inserts are supplied to surgeons with the reinforcement pin preassembled within the insert. The pin is positioned within the insert by simply placing the proximal portion of the pin within the bore and then forcing the ribbed region of the reinforcement pin into the bore to create an interference fit. Preferably, the pin is fully inserted into the tibial bearing insert such that the proximal tip of the pin contacts the end wall of the bore. It will be apparent to those having ordinary skill in the art that the construction of the ribbed region is such that the canted proximal facing surfaces 54 of the ribs are able to be forced within the bore. Because the pin is made from a material that is harder than the polymer from which the tibial bearing insert is made, the pin is able to deform the bore without deforming the ribs. When the pin is fully inserted within the bore, material from which the tibial bearing insert is made tends to surround the ribs. The distal facing surface 56 of the ribs is of such a construction, as described above, such that the pin is substantially permanently disposed within the bore. That is, the polymer material which forms around the ribs anchors the pin within the material such that only extremely high forces are able to dislodge the pin from the insert. Generally, the insert will be destroyed in the course of attempting to remove the pin therefrom.

Once the reinforcement pin 20 is disposed within the tibial bearing insert, a distal portion of the pin protrudes from the inferior surface of the tibial bearing insert. The tibial bearing insert can then be mated to the tibial tray by positioning the protruding distal end of the pin within bore 42 formed in the tibial tray and then forcing the tibial tray and the tibial bearing insert together to activate an interlocking mechanism that binds these two components together in a mechanical fit. Those of ordinary skill in the art will be readily appreciate that various types of interlocking elements may be present on the tibial bearing insert and the tibia tray to mechanically engage these components to one another.

Approximately one-half to two-thirds of the pin 20 is disposed within the tibial bearing insert. The remainder of the pin protrudes from the inferior surface of the insert and can be placed within bore 42 of the tibial tray.

As noted above, the diameter of bore 42 is substantially the same as the diameter of bore 40. Thus, the distal end of pin 20 may be disposed within bore 42 in a clearance fit. Preferably, the clearance is in the range of 0.001 to 0.005 inch. The portion of the pin disposed within bore 42 is not mechanically engaged therein. Rather, it is disposed within bore 42 in a floating fit. FIG. 3 illustrates the engagement of a tibial bearing insert having a reinforcement pin secured therein within a tibial tray.

Reinforcement pin 20 provides increased strength to the tibial bearing insert and renders it less susceptible to adverse effects that may be caused by anteriorally directed components of forces placed on the tibia bearing member by the femoral component. Thus, the tibial bearing insert is rendered more stable and it enables a tighter, more secure fit between the tibial bearing insert and the tibial tray. The pin also serves to absorb some of the load exerted by the femoral component and transfers the load to the tibial tray. This is advantageous since the tibial tray and the reinforcement pin are made of materials, such as metal alloys, that are stronger than the polymeric tibia bearing insert.

The tibial bearing insert and the tibial tray can be made of materials that are well known in the art. The tibial bearing insert is typically made of a polymeric material, such as ultra high molecular weight polyethylene (UHMWPE), while the tibial tray is typically made of a titanium alloy. The reinforcement pin preferably is made of a metal alloy as well, such as a titanium alloy. Preferably the reinforcement pin is made of the same material used to manufacture the tibial tray.

Those having ordinary skill in the art will appreciate that the components of the knee joint prosthesis of the invention may be of various dimensions that are suitable to fit the anatomies of a variety of patients. Similarly, the dimensions of the reinforcement pin of the invention may vary and can be determined by one of ordinary skill in the art. Generally, however, the reinforcement pin has a length of about 1.3 to 2.2 inches, depending upon the size of the tibial tray and tibial bearing insert with which it is to be used. The diameter of a non-ribbed portion of the pin can vary between about 0.250 and 0.260 inch, and preferably is about 0.258 inch. The diameter of the ribbed region of the pin can be between about 0.251 and 0.275 inch, and preferably is about 0.263 to 0.268 inch. A bore of diameter suitable to properly accommodate a pin having the dimensions described above should be in the range of about 0.252 to 0.272 inch, and most preferably about 0.260 inch.

In a preferred embodiment the proximal end of ribbed region 50 begins about 0.15 to 0.40 inch distal of the proximal tip of the pin and extends for a distance of approximately 0.15 to 0.40 inch. The axial distance spanned by each rib may vary depending on factors such as ribbed region diameter and rib angle (α). Preferably, each rib spans an axial distance of approximately 0.035 to 0.050 inch and most preferably about 0.041 inch.

It will be appreciated by those having ordinary skill in the art that the knee prosthesis of the invention can be made from a variety of biocompatible materials having high strength, durability and resistance to wear debris. Examples of such material include metal alloys such as cobalt chromium alloy, titanium aluminum vanadium alloy, stainless steel, ceramics, and other materials that are well known for use in the manufacture of implantable bone prostheses. Typically, the femoral component and tibial tray are made from metal alloys such as cobalt chromium alloy while the tibial bearing member is made from polymers such as ultrahigh molecular weight polyethylene. The reinforcement pin and the tibial tray generally are made of the same metal alloy.

EXAMPLE

Tests were conducted to determine the frictional resistance to pull out of certain reinforcement pins mounted within polyethylene inserts. Test inserts made of ultrahigh molecular weight polyethylene were provided. Each insert had a bore with a diameter of approximately 0.260 inch. Reinforcement pins having the diameter noted below in Table 1 were inserted within the bore of the inserts. While the inserts were secured, axial load was applied to the pins to determine the force required to remove the pin from the insert. Pin numbers 1 and 2 were constructed according to the teachings of the present invention having a diameter, in the ribbed region, of approximately 0.265 inch. Pin number 3 was also constructed according to the present invention and had a diameter, in the ribbed region, of approximately 0.268 inch. Pin number 4 was constructed with axially oriented knurls with a diameter in the knurled region of approximately 0.265 inch. The data obtained is illustrated in Table 1.

TABLE 1

| Pin | Peak Pull-out Load (Kg) |
| --- | --- |
| 1 | 75.8 |
| 2 | 95.2 |
| 3 | 122.1 |
| 4 | 19.8 |

The foregoing description of the invention is presented to indicate the range of constructions to which the invention applies. Variations in the physical architecture and dimensions of the components of the knee prosthesis of the invention will be apparent to those having ordinary skill in the art based upon the disclosure herein and such variations are considered to be within the scope of the invention in which patent rights are asserted as set forth in the claims pended hereto. The entirety of all references cited herein is expressly incorporated by reference.

What is claimed is:

1. A knee joint prosthesis, comprising:
   a tibial tray component having an inferior surface adapted to mount within the tibia of a patient and an opposed superior surface including a first mating means for mechanically joining the tibial tray to a tibial bearing insert;
   a tibial bearing insert having a superior bearing surface with condylar portions adapted to seat condyle elements of a femoral component of a knee prosthesis, and an opposed inferior surface having second mating means for mechanically joining the tibial bearing insert within the superior surface of the tibial tray component;
   a first bore extending partially into the tibial bearing insert from the inferior surface of the bearing insert;
   an elongate reinforcement pin having a first, proximal end that is spherically shaped and a second, distal end, the pin including a ribbed region having at least one circumferentially oriented rib disposed distally of the first end, and an axial break in the ribbed region forming a discontinuity in each rib, the pin being configured to mount at least partially within the bore such that the ribbed region interferingly engages the tibial insert.

2. The prosthesis of claim 1 further including a second bore formed in the superior surface of the tibial tray, the first and second bores being aligned with each other when the tibial bearing insert is mated to the tibial tray component.

3. The prosthesis of claim 1 wherein the ribs are axially spaced from one another and each rib has a canted proximal facing surface and a distal facing surface that is substantially transverse to a longitudinal axis of the pin.

4. The prosthesis of claim 3 wherein the angle of the canted surfaces of each rib, as measured from an exterior wall of the pin proximal to the ribs, is in the range of about 110° to 175°.

5. The prosthesis of claim 1 wherein the diameter of the ribbed region of the pin exceeds the diameter of the non-ribbed region of the pin that is disposed proximal of the ribbed region.

6. The prosthesis of claim 1 wherein the diameter of the pin in the ribbed region exceeds the diameter of the pin in the non-ribbed region.

7. The prosthesis of claim 6 wherein the diameter of the ribbed region of the prosthesis exceeds the diameter of the non-ribbed region of the pin by about 0.001 to 0.017 inch.

8. The prosthesis of claim 1 wherein the first end of the pin is spherically shaped.

9. The prosthesis of claim 3 wherein the pin has from 1 to about 15 ribs.

10. The prosthesis of claim 1 wherein the superior surface of the tibial bearing insert includes a raised eminence.

11. The prosthesis of claim 10 wherein the first bore extends at least partially into the portion of the tibial bearing insert that defines the raised eminence.

12. The prosthesis of claim 2 wherein the first and second bores are of substantially equal diameter.

13. The prosthesis of claim 1 wherein the pin is of sufficient length that at least a portion of the second end of the pin protrudes from the inferior surface of the tibial bearing insert when the pin is mounted within the first bore.

14. The prosthesis of claim 13 wherein the second end of the pin that protrudes from the inferior surface of the tibial bearing insert is adapted to seat within the second bore when the tibial bearing insert is mated with the tibial tray.

15. The prosthesis of claim 1 wherein the first bore is aligned substantially at the midpoint between medial and lateral edges of the tibial bearing insert.

* * * * *